(12) United States Patent
Barbier et al.

(10) Patent No.: US 6,316,410 B1
(45) Date of Patent: Nov. 13, 2001

(54) PARATHYROID HORMONE ANALOGUES FOR THE TREATMENT OF OSTEOPOROSIS

(75) Inventors: Jean-René Barbier, Gatineau; Paul Morley; James F. Whitfield, both of Ottawa; Gordon E. Willick, Orleans, all of (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/406,813

(22) Filed: Sep. 22, 1999

(51) Int. Cl.$^7$ .............................. A61K 38/00; C07K 5/00; C07K 7/00
(52) U.S. Cl. ..................................... 514/12; 514/2; 514/9; 514/11; 530/317; 530/324; 530/345; 424/185.1
(58) Field of Search ............................... 514/11, 12, 21; 530/317, 324, 345; 424/185.1

(56) References Cited

U.S. PATENT DOCUMENTS

| | | | |
|---|---|---|---|
| 5,556,940 | * | 9/1996 | Willick et al. ..................... 530/317 |
| 6,110,892 | * | 8/2000 | Barbier et al. ..................... 514/11 |

FOREIGN PATENT DOCUMENTS

| | | | |
|---|---|---|---|
| 195 08 672 A | | 9/1996 | (DE) . |
| WO96 40193 A | | 12/1996 | (WO) . |
| WO98 05683 A | | 2/1998 | (WO) . |
| WO98 51324 A | | 11/1998 | (WO) . |

OTHER PUBLICATIONS

Whitfield J F, et al "Cyclization by a specific lactam increases the ability of human parathyroid hormone (hPTH)–(1–31)NH–2 to stimulate bone growth in ovariectomized rats" Journal of Bone and Mineral Research, vol. 12, No. 8, 1997, pp. 1246–1252, XP000989742 ISSN: 0884–0431.

Whitfield J F, et al: "Comparison of the abilities of human parathyroid hormone (hPTH)–(1–34) and (Leu27)–cyclo(Glu22–Lys26)–hPTH–(1–31)NH2 to stimulate femoral trabecular bone growth in ovariectomized rats" Calcified Tissue International, vol. 63, No. 5, Nov. 1998 (1998–11) pp. 423–428, XP000989576 ISSN 0171–967x.

Barbier E A: "Bioactivities and Secondary structures of constrained analogues of Human Parathyroid Hormone: Cyclic Lactams of the receptor binding region" Journal of Medicinal Chemistry, American Chemical Society. Washington, US, vol. 40 1997, pp. 1373–1380, XP002147862 ISSN: 0022–2623.

Whitfield J F, et al: "The stimulation of vertebral and tibial bone growth by the parathyroid hormone framents, hPTH–(1–31)NH2, (Leu27)cyclo(Glu22–Lys26)hPTH–(1–3 1)NH2, and hPTH–(1–30)NH2" Calcified Tissue International, vol. 66, No. 4, Apr. 2000 (2000–04), pp. 307–312, XP000989575 ISSN: 0171–967X.

Whitfield J F, et al: "Lactam formation increases receptor binding, adenylyl cyclase stimulation and bone growth stimulation by human parathyroid hormone (hPTH)(1–28)NH2." Journal of Bone and Mineral Research, vol. 15, No. 5, May 2000 (2000–05), pp. 964–970, XP000989584 ISSN: 0884–0431.

* cited by examiner

*Primary Examiner*—Avis M. Davenport
(74) *Attorney, Agent, or Firm*—J. Wayne Anderson

(57) ABSTRACT

The invention disclosed relates to analogues of human parathyroid hormoneh(PTH) which have increased activities in bone restoration, and increased bioavailablities. The analogues described are either single cyclic (1–28) or (1–29) analogues, or double cyclic (1–28) to (1–31) analogues. The single cyclic analogues are cyclised between amino acid pairs R22 and R26. The double cyclic analogues are cyclised between amino acid pairs 13 and 17, and 22 and 26. Various substitutions of the natural residues for other amino acids are also described. For example, the natural Lys27 residue may be substituted by Leu. Typically, these novel analogues have enhanced abilities to stimulate adenyl cyclase activity in rat osteosarcoma cells, and show increased activities in bone restoration using the ovariectomized rat model.

22 Claims, 4 Drawing Sheets

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Gln-Asp-Val-His-Asn-Phe-COOH

Fig. 1

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Gln-Asp-Val-NH₂

Fig. 2

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-NH₂

Fig. 3

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Leu-Gln-NH₂

Fig. 4

H₂N-Ser-Val-Ser-Glu-Ile-Gln-Leu-Met-His-Asn-Leu-Gly-Lys-His-Leu-Asn-Glu-Met-Glu-Arg-Val-Glu-Trp-Leu-Arg-Lys-Leu-Leu-Gln-Asp-Val-NH₂

Fig. 5

H₂N-Ser-Val-Ser-Glu-Ile-Gln-Leu-Met-His-Asn-Leu-Gly-Lys-His-Leu-Asn-Glu-Met-Glu-Arg-Val-Glu-Trp-Leu-Arg-Lys-Leu-Leu-NH₂

Fig. 6

SEQUENCE LISTING

<160> NUMBER OF SEQ ID NOS: 9

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 2
<211> LENGTH: 31
<212> TYPE: PRT
<213> ORGANISM: Homo sapiens
<220> FEATURE:
<223> OTHER INFORMATION: This sequence has an amino group c-terminus
      (NH2).

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
                20                  25                  30

<210> SEQ ID NO 3
<211> LENGTH: 28
<212> TYPE: PRT
<213> ORGANISM: Homo sapiens
<220> FEATURE:
<223> OTHER INFORMATION: Cyclo Glu22-Lys 26, and this sequence has an
      amino group c-terminus (NH2).

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Leu Leu
                20                  25

<210> SEQ ID NO 4
<211> LENGTH: 29
<212> TYPE: PRT
<213> ORGANISM: Homo sapiens
<220> FEATURE:
<223> OTHER INFORMATION: Cyclo Glu22-Lys 26, and this sequence has an
      amino group c-terminus (NH2).

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln
                20                  25

<210> SEQ ID NO 5
<211> LENGTH: 31
<212> TYPE: PRT
<213> ORGANISM: Homo sapiens
<220> FEATURE:
<223> OTHER INFORMATION: Cyclo Lys13-Glu17, cyclo Glu22-Lys 26, and this
      sequence has an amino group c-terminus (NH2).

<400> SEQUENCE: 5

Ser Val Ser Glu Ile Gln Leu Met His Asn Leu Gly Lys His Leu Asn
1               5                   10                  15

Glu Met Glu Arg Val Glu Trp Leu Arg Lys Leu Leu Gln Asp Val
                20                  25                  30

<210> SEQ ID NO 6
<211> LENGTH: 28

```
<212> TYPE: PRT
<213> ORGANISM: Homo sapiens
<220> FEATURE:
<223> OTHER INFORMATION: Cyclo Lys13-Glu17, cyclo Glu22-Lys 26, and this
      sequence has an amino group c-terminus (NH2).

<400> SEQUENCE: 6

Ser Val Ser Glu Ile Gln Leu Met His Asn Leu Gly Lys His Leu Asn
 1               5                  10                  15

Glu Met Glu Arg Val Glu Trp Leu Arg Lys Leu Leu
            20                  25

<210> SEQ ID NO 7
<211> LENGTH: 31
<212> TYPE: PRT
<213> ORGANISM: Homo sapiens
<220> FEATURE:
<222> LOCATION: (1)
<223> OTHER INFORMATION: Ser, Ala or Aib
<222> LOCATION: (8)
<223> OTHER INFORMATION: Met, Nle or a naturally occuring hydrophobic
      amino acid
<222> LOCATION: (13)
<223> OTHER INFORMATION: Lys, Orn, Glu, Asp, Cys or Hcys
<222> LOCATION: (14)
<223> OTHER INFORMATION: His or a water soluble amino acid
<222> LOCATION: (15)
<223> OTHER INFORMATION: Leu or a water soluble amino acid
<222> LOCATION: (16)
<223> OTHER INFORMATION: Asn or a water soluble amino acid
<222> LOCATION: (17)
<223> OTHER INFORMATION: Ser, Glu, Asp, Lys, Orn, Cys, Hcys or a
      water soluble amino acid
<222> LOCATION: (18)
<223> OTHER INFORMATION: Met, Nle or a naturally occuring hydrophobic
      amino acid
<222> LOCATION: (22)
<223> OTHER INFORMATION: Glu, Lys, Orn, Cys, Asp or Hcys
<222> LOCATION: (25)
<223> OTHER INFORMATION: Arg or His
<222> LOCATION: (26)
<223> OTHER INFORMATION: Lys, Orn, Glu, Cys, Asp or Hcys
<222> LOCATION: (27)
<223> OTHER INFORMATION: Lys, Leu or a naturally occurring hydrophobic
      or polar amino acid
<223> OTHER INFORMATION: This peptide may also encompass a sequence
      wherein the c-terminus ends with Gln or Gln-Asp, and this sequence
      may also have a c-terminus NHR (R = hydrogen or any linear
      or branched chain alkyl, acyl or aryl group).

<400> SEQUENCE: 7

Xaa Val Ser Glu Ile Gln Leu Xaa His Asn Leu Gly Xaa Xaa Xaa Xaa
 1               5                  10                  15

Xaa Xaa Glu Arg Val Xaa Trp Leu Xaa Xaa Xaa Leu Gln Asp Val
            20                  25                  30

<210> SEQ ID NO 8
<211> LENGTH: 29
<212> TYPE: PRT
<213> ORGANISM: Homo sapiens
<220> FEATURE:
<222> LOCATION: (8)
<223> OTHER INFORMATION: Met or Nle
<222> LOCATION: (18)
<223> OTHER INFORMATION: Met or Nle
<222> LOCATION: (22)
<223> OTHER INFORMATION: Glu, Asp, Lys, Orn, Cys or Hcys
<222> LOCATION: (25)
<223> OTHER INFORMATION: Arg or His
<222> LOCATION: (26)
<223> OTHER INFORMATION: Glu, Asp, Lys, Orn, Cys or Hcys
<222> LOCATION: (27)
<223> OTHER INFORMATION: Lys, Leu, Ala, or Nle
```

```
<223> OTHER INFORMATION: This peptide may also encompass a sequence
      wherein the c-terminus ends with Leu, and this sequence may also
      have a c-terminus NHR (R = hydrogen or any linear
      or branched chain alkyl, acyl or aryl group).

<400> SEQUENCE: 8

Ser Val Ser Glu Ile Gln Leu Xaa His Asn Leu Gly Lys His Leu Asn
 1               5                  10                  15

Ser Xaa Glu Arg Val Xaa Trp Leu Xaa Xaa Xaa Leu Gln
            20                  25

<210> SEQ ID NO 9
<211> LENGTH: 31
<212> TYPE: PRT
<213> ORGANISM: Homo sapiens
<220> FEATURE:
<222> LOCATION: (8)
<223> OTHER INFORMATION: Met or Nle
<222> LOCATION: (13)
<223> OTHER INFORMATION: Lys, Orn, Glu, Asp, Cys or Hcys
<222> LOCATION: (17)
<223> OTHER INFORMATION: Lys, Orn, Glu, Asp, Cys or Hcys
<222> LOCATION: (18)
<223> OTHER INFORMATION: Met or Nle
<222> LOCATION: (22)
<223> OTHER INFORMATION: Glu, Asp, Lys, Orn, Cys or Hcys
<222> LOCATION: (25)
<223> OTHER INFORMATION: Arg or His
<222> LOCATION: (26)
<223> OTHER INFORMATION: Lys, Orn, Glu, Asp, Cys or Hcys
<222> LOCATION: (27)
<223> OTHER INFORMATION: Lys, Leu, Nle or a naturally occurring
      hydrophobic or polar amino acid.
<223> OTHER INFORMATION: This peptide may also encompass a sequence
      wherein the c-terminus ends with Gln or Gln-Asp, and this sequence
      may also have a c-terminus NHR (R = hydrogen or any linear
      or branched chain alkyl, acyl or aryl group).

<400> SEQUENCE: 9

Ser Val Ser Glu Ile Gln Leu Xaa His Asn Leu Gly Xaa His Leu Asn
 1               5                  10                  15

Xaa Xaa Glu Arg Val Xaa Trp Leu Xaa Xaa Xaa Leu Gln Asp Val
            20                  25                  30
```

PARATHYROID HORMONE ANALOGUES FOR THE TREATMENT OF OSTEOPOROSIS

CROSS-REFERENCE TO RELATED APPLICATION

This application relates to U.S. application Ser. No. 08/904,760, filed 1 Aug., 1997.

FIELD OF THE INVENTION

This invention relates to analogues of human parathyroid hormone, which have been found to be effective in the treatment of osteoporosis.

BACKGROUND OF THE INVENTION

Osteoporosis is a leading cause of disability in the elderly, particularly elderly women. It has recently been realized that human parathyroid hormone (hPTH) and certain analogues are stimulators of bone growth that are useful in the treatment of osteoporosis. Osteoporosis is a progressive disease which results in the reduction of total bone mass and increased bone fragility. This often results in spontaneous fractures of load-bearing bones and the physical and mental deterioration characteristic of immobilizing injuries. Postmenopausal osteoporosis is caused by the disappearance of estrogens which trigger a decade-long acceleration of bone turnover with an increased imbalance between resorption of old bone and formation of new bone. This results in thinning, increased porosity, and trabecular depletion of load-bearing bones. Osteoporosis is also associated with hyperthyroidism, hyperparathyroidism, Cushing's syndrome, and the use of certain steroidal drugs. Remedies historically have involved increase in dietary calcium, estrogen therapy, and increased doses of vitamin D, but mainly with agents such as antiresorptives that inhibit bone resorption by osteoclasts.

Parathyroid hormone (PTH) is produced by the parathyroid gland and is a major regulator of blood calcium levels. PTH is a polypeptide and synthetic polypeptides may be prepared by the method disclosed by Erickson and Merrifield, The Proteins, Neurath et al., Eds., Academic Press, N.Y., 1976, page 257, and as modified by the method of Hodges et al (1988) Peptide Research 1, 19 or by Atherton, E. And Sheppard, R. C. Solid Phase Peptide Synthesis, IRL Press, Oxford, 1989.

When serum calcium is reduced to below a normal level, the parathyroid gland releases PTH and the calcium level is increased by resorption of bone calcium, by increased absorption of calcium in from the intestine, and by increased renal reabsorption of calcium front nascent urine in the kidney tubules. Although continuously infused low levels of PTH can remove calcium from the bone, the same low doses, when intermittently injected can actually promote bone growth.

Tregear, U.S. Pat. No. 4,086,196, described human PTH analogues and claimed that the first 27 to 34 amino acids are the most effective in terms of the stimulation of adenylyl cyclase in an in vitro cell assay. Rosenblatt, U.S. Pat. No. 4,771,124, disclosed the property of hPTH analogues wherein $Trp^{23}$ is substituted by amino acids phenylalanine, leucine, norleucine, valine, tyrosine, β-napthylalanine, or α-napthylalanine as a PTH antagonist. These modified hPTH analogues also have the 2 and 6 amino terminal acids removed, resulting in loss of most agonist activities when used to treat osteoporosis. These analogues were designed as inhibitors of PTH and PTH-related peptide. The analogues were claimed as possibly useful in the treatment of hypercalcemia associated with some tumors.

Pang et al, WO93/06845, published Apr. 15, 1993, described analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine, or valine. These are claimed, with no supporting data from animal or human trials, to be effective in the treatment of osteoporosis with minimal effects on blood pressure and smooth muscle.

Other references of interest which disclose hPTH analogues are PCT published application no. WO9851324, of Condon and Morze, U.S. Pat. No. 5,747,456 of Chorev et al., and U.S. Pat. No. 5,717,062 of Rosenblatt et al., which disclose some single and double cyclics involving 13–17 and 26–30 cyclizations.

PTH operates through activation of two second messenger systems, $G_s$-protein activated adenylyl cyclase (AC) and $G_q$-protein activated phospholipase $C_\beta$. The latter results in a stimulation of membrane-bound protein kinase Cs (PKC) activity. In a rat osteosarcoma(RCO) cell line the PKC activity has been shown to require PTH residues 29 to 32 (Jouishomme et al (1994) J. Bone Mineral Res. 9, (1179–1189). It has been established that the increase in bone growth, i.e. that effect which is useful in the treatment of osteoporosis, is coupled to the ability of the peptide sequence to increase AC activity. The native h(PTH)-(1–34) sequence has been shown to have all of these activities. The hPTH-(1–34) sequence is typically shown as (A):

Ser Val Ser Glu Ile Gln Leu Met His Asn Leu Gly Lys His Leu Asn Ser Met Glu Arg Val Glu Trp Leu Arg Lys Lys Leu Gin Asp Val His Asn Phe-OH (SEQ ID NO: 1) A

The following linear analogue, hPTH-(1–31)-$NH_2$, has only AC-stimulating activity and has been shown to be fully active in the restoration of bone loss in the ovariectomized rat model (Rixon, R. H. et al (1994) J. Bone Miner. Res. 9, 1179–1189; Whitfield et al (1996), Calcified Tissue Int 58, 81–87; Willick et al, U.S. Pat. No. 5,556,940 issued Sep. 17, 1996):

Ser Val Ser Glu Ile Gln Leu Met His Asn Leu Gly Lys His Leu Asn Ser Met Glu Arg Val Glu Trp Leu Arg Lys Lys Leu Gin Asp Val-$NH_2$ (SEQ ID NO: 2) B

The above molecule, B, may have a free carboxyl ending instead of the amide ending illustrated.

It is an object of the present invention to produce new PTH analogues with greater metabolic stability, increased bone restoration activity, increased AC activity, and minimal clinical side effects.

BRIEF SUMMARY OF THE INVENTION

According to one aspect of the invention, novel human parathyroid hormone (hPTH) analogs, and pharmaceutically acceptable salts thereof are provided, having the amino acid sequence R-NH-R1-Val-Ser-Glu-Ile-Gln-Leu-R8-His-Asn-Leu-Gly-R13-R14-R15-R16-R17-R18-Glu-Arg-Val-R22-Trp-Leu-R25-R26-R27-Leu-Y (SEQ ID NO: 7)

wherein,

R=hydrogen or any linear or branched chain alkyl, acyl or aryl group,

R1=Ser, Ala or Aib,

R8=Met, NLe or a naturally occurring hydrophobic amino acid,

R13=Lys, Orn, Glu, Asp, Cys or Hcys(homocysteine),

R14=His or a water soluble amino acid,
R15=Leu or a water soluble amino acid,
R16=Asn or a water soluble amino acid,
R17=Ser, Glu, Asp, Lys, Orn, Cys, Hcys(homocysteine) or a water soluble amino acid,
R18=Met, Nle or a naturally occuring hydrophobic amino acid,
R22=Glu, Lys, Orn, Cys, Asp or Hcys(homocysteine),
R25=Arg or His,
R26=Lys, Orn, Glu, Cys, Asp or Hcys,
R27=Lys, Leu or a naturally occurring hydrophobic or polar amino acid,
X=OR or NHR,
Y=X, Gln-X, Gln-Asp-X, or Gln-Asp-Val-X,
provided that when Y=X or Y=Gln-X, cyclized between one or two amino acid pairs R13 and R17 and R22 and R26, and
when Y=Gln-Asp-X or Y=Gln-Asp-Val-X, cyclized between two amino acid pairs R13 and R17 and R22 and R26, each amino acid in said amino acid pairs having a side chain enabling the formation of either a lactam or a disulfide bridge between the side chains thereof.

According to a preferred aspect of the invention, novel hPTH analogs and pharmaceutically acceptable salts thereof are provided, having the amino acid sequence
R-NH-Ser-Val-Ser-Glu-Ile-Gln-Leu-R8-His-Asn-Leu-Gly-Lys- His-Leu-Asn-Ser-R18-Glu-Arg-Val-R22-Trp-Leu-R25-R26-R27-Leu-Y (SEQ ID NO: 8)
wherein,
R=hydrogen or any linear or branched chain alkyl, acyl, or aryl group,
R8=Met or Nle,
R18=Met or Nle,
R22=Glu, Asp, Lys, Orn, Cys or Hcys,
R25=Arg or His,
R26=Glu, Asp, Lys, Orn, Cys or Hcys,
R27=Lys, Leu, Ala or Nle,
Y=X or Gln-X, and
X=OR or NHR, cyclized between amino acid pairs R22 and R26, each amino acid in said amino acid pairs having a side chain enabling the formation of either a lactam or a disulfide bridge between the side chains thereof.

According to another preferred aspect of the invention novel double cyclic hPTH analogs and pharmaceutically acceptable salts thereof are provided, having the amino acid sequence
RNH-Ser-Val-Ser-Glu-Ile-Gln-Leu-R8-His-Asn-Leu-Gly-R13-His-Leu-Asn-R17-R18-Glu-Arg-Val-R22-Trp-Leu-R25-R26-R27-Leu-Y (SEQ ID NO: 9)
wherein,
R=hydrogen or any linear or branched chain alkyl, acyl or aryl group,
R8=Met or Nle,
R13=Lys, Orn, Glu, Asp, Cys or Hcys,
R17=Lys, Orn, Glu, Asp, Cys or Hcys,
R18=Met or Nle,
R22=Glu, Asp, Lys, Orn, Cys or Hcys,
R25=Arg or His,
R26=Lys, Orn, Glu, Asp, Cys or Hcys,
R27=Lys, Leu, Nle or a naturally occurring hydrophobic or polar amino acid,
Y=X, Gln-X, Gln-Asp-X or Gln-Asp-Val-X,
X=OR or NHR,
cyclised between two amino acid pairs R13 and R17 and R22 and
R26, each amino acid residue R13 and R17 having a side chain which enables formation of either a lactam or a disulfide bridge between the side chains thereof, and each amino acid residue R22 and R26 having a side chain which enables formation of either a lactam or a disulfide bridge between the side chains thereof.

Examples of the salts include salts of inorganic acids, salts of organic acids such as formic acid, acetic acid, tartaric acid and citric acid, salts of inorganic bases such as sodium and ammonium and salts of organic bases such as triethylamine, ethylamine and methylamine.

According to another feature of the present invention, cyclisation is effected by the formation of lactams, involving the coupling of the side-chains of the selected amino acid pairs such as between residues 22 and 26. Other types of cyclisations, such as the formation of a disulfide bridge e.g. between Cys containing analogues $Cys^{22}$-$Cys^{26}$ are also contemplated.

Substitutions of various amino acids have also been found to be effective. $Lys^{27}$ may be replaced by a Leu or by various other naturally occuring hydrophobic or polar residues. Another factor is how well the residue fits to the receptor. Ala is not as hydrophobic as Leu. Lys and Tyr are generally considered to be polar, but nonetheless have hydrophobic interactions with the receptor. Lys, for example, can fold so that the hydrophobic part interacts with hydrophobic residues or portions of residues in the PTH receptor, and its side chain $NH_2$ functional group remains exposed to solvent. Possible substitutions for Lys, other than the preferred Leu, include such polar residues as omithine and citrulline, and hydrophobic ones such as alanine, norleucine, isoleucine and tyrosine, or any linear or branched α-amino aliphatic acid, having 2–10 carbons in the side chain, and any such analogue having a polar or charged group at the terminus of the aliphatic chain. Examples of polar or charged groups include: amino, carboxyl, acetamido, guanido and ureido. Although it appears that $Leu^{27}$ is the best substitution, it also appears that many other pos27 substitutions retain nearly full activity and could also have desired properties, such as increased proteolytic stability or water solubility. Ile, norleucine, Met, and ornithine are expected to be the most active.

We have shown that although any analogue containing at least the N-terminal 28 residues of PTH has adenyl cyclase-stimulating activity(Neugebauer, W., Barbier, J. R., Sung, W. L., Whitfield, J. F., Willick, G. E.(1995), "Solution structure and adenyl cyclase-stimulating activities of C-terminal truncated human parathyroid hormone analogues", Biochemistry, 34: 8835–8842), full anabolic activity in the linear natural sequerie requires at least the N-terminal 31 residues (Whitfield, J. F., Morley, P., Willick, G. E., Ross, V., Barbier, J. R., Isaacs, R. J., and Ohannessian, Barry L., (1996) "Stimulation of the growth of femoral trabecular bone in ovariectomized rats by the novel parathyroid hormone fragment, hPTH(1–31 )NH2 (Ostabolin)", Calcif. Tissue Int. 58: 81–87) and that anabolic stimulation was possible with hPTH(1–30)NH2, but only with much higher doses than used with the (1–31) analogue(Whitfield, J. F., Morley, P., Willick, G. E., MacLean, S., Ross, V., Barbier, J. R., and Isaacs, R. J., (1999) "Stimulation of femoral trabecular bone in ovariectomized rats by human parathyroid hormone hPTH(1–30)NH2", Calc. Tiss. Int., 65: 143–147). Thus we expected that the still shorter linear analogues hPTH(1–28) and hPTH(1–29) would also have only weak anabolic activity. The low activity of hPTH(1–28) $NH_2$ is shown in an Example that follows.

Further, we now have evidence, included in the Examples that follow, that substitution of Lys-27 with Leu, and the formation of a lactam between residues 22 and 26, brings adenyl cyclase-stimulating activity to a level comparable to hPTH(1–34) and also brings the anabolic(bone growth-stimulating) activity to a level comparable to that of hPTH (1–34).

NMR studies have shown that even a model peptide found to be highly helical by CD also populates many non-helical conformations. Thus, the structure of a receptor-bound peptide hormone, such as PTH, cannot be inferred reliably from its free structure in solution. Constrained analogues of peptide hormones have been used to limit the number of conformational states available to the peptide. Examination of the sequence of hPTH reveals 3 possible salt bridges within residues 17–29 which could either stabilize or destabilize α-helix. These are between $Glu^{22}$ and $Lys^{26}$, and $Lys^{26}$ and $Asp^{30}$, both of which are expected to stabilize an α-helix, and between $Lys^{27}$ and $Asp^{30}$, which is expected to destabilize an α-helix.[4] Lactam formation between these residue pairs would restrict the conformations available to hPTH in this helical region. Furthermore, two of these lactams, $Glu^{22}$-$Lys^{26}$ and $Lys^{26}$-$Asp^{30}$ which are expected to stabilize α-helical structure are located on the polar face of the amphiphilic portion of the α-helix. The third one, $Lys^{27}$-$Asp^{30}$, is expected to at least partially destabilize α-helix and involves a residue, $Lys^{27}_1$, which is on the hydrophobic face of the amphiphilic helix bounded by residues 21–31. Cyclisation as a lactam between positions 25 and 29 can also occur if Lys or Orn replaces Arg in position 25, and if $Gln^{29}$ is replaced with Glu or Asp.

The substitution of Leu for the $Lys^{27}$ results in a more hydrophobic residue on the hydrophobic face of the amphiphilic helix. This resulted in increased adenylyl cyclase stimulating activity in the ROS cel line. It will be appreciated by those skilled in the art that other such substitutions discussed above would likely result in analogues with the same or increased activities.

The combined effect of substitution and lactam formation is expected to stabilize the α-helix and increase bioactivity, and to protect this region of the molecule from proteolytic degradation. The presence of the amide at the C-terminus is preferred in the sense that it is further expected to protect the peptide against exoproteolytic degradation, although some peptidases can hydrolyze them. (Leslie, F. M. and Goldstein, A. (1982) *Neuropeptides* 2, 185–196).

It has also been found that other amino acid substitutions can usefully be made. Specifically, we have replaced the oxidation sensitive Met residue at positions 8,18 with a naturally occuring hydrophobic residue, Nle, as per Japanese Patent publication 61-24598. It is also to be expected that other such hydrophobic residues like Leu, Ile, Val, Phe and Trp would also be useful, as per U.S. Pat. No. 5,393,869 to Nakagawa et al.

Reverse lactams are also contemplated. For example, we have shown the effectiveness of a 22-26 switch e.g. a $Lys^{22}$-$Glu^{26}$ switch. It is therefore to be expected that similar switches could be usefully made as between other lactams e.g. the 13–17 lactams.

In U.S. Pat. No. 5,393,869 Nakagawa et al and U.S. Pat. No. 5,434,246, Fukuda et al some substituted hPTH analogues were reported to have substantial AC activity and might have enhanced stabilities to proteolytic attack, specifically, 1. Ser-1 to Aib (α-aminoisobutyric acid)
2. Lys-27 to Gln (reported to have 2.5×AC activity)
3. Residues 14, 15, 16, 17 to Lys, in whole or in part reported to greatly increase activity—up to 8X. (This may be due to increase in water solubility. In vivo, these are expected to be more labile to trypsin-like enzymes). They claim this tetrapeptide (residues 14–17, incl.) such that there is at least one water soluble amino acid. Possibilities include His-14 or Lys-14; Leu-15, Lys-15 or Arg-15; Asn-16, Orn-16, HCi-16, Asp-16, Arg-16, Lys-16, D-Dlys-16, Ser-16 or Gly-16; and Ser-17, Lys-17, Asp-17, Arg-17 or Glu-17. Since our lactams, particularly with Leu or another hydrophobic amino acid at position-27, can become somewhat insoluble and also difficult to dissolve, it would be expected that the same substitutions would be useful in our lactams.
4. Arg 25 to His to minimize protease attack It will also be appreciated by those skilled in the art that although the 1–28 hPTH cyclic may be preferred, it is to be expected from the data presented herein that cyclic 1–29 fragments will also be effective. In particular, there is no evidence in the literature that the presence of the additional amino acid would affect the biological properties of the hormone, particularly given the confirmatory 1–30 to 1–34 data included in our prior U.S application Ser. No. 08/904, 760, the Disclosure of which is incorporarted herein by reference.

It has also been found that analogues having two cyclisations are quite active in stimulating adenyl cyclase in cell cutures. One such analogue includes a lactam cyclisation between residues 22 and 26 and another between residues 13 and 17. An example is an hPTH molecule with two separate cyclizations, Glu22-Lys26 and Lys13-Glu17, and a preferable Leu27 substitution. Such an analogue, even if not more active in AC-stimulation, may be preferable, for example, in oral delivery.

The analogues according to the invention may be prepared by known procedures described below, and may be used for stimulating bone growth, for restoring bone, and for the promotion of bone healing in various circumstances, such as in the treatment of osteoporosis and normal fractures.

BRIEF DESCRIPTION OF THE DRAWINGS

FIG. 1 shows the structure of natural hPTH, residues 1–34. (SEQ ID NO: 1);

FIG. 2 shows the structure of natural hPTH-$NH_2$, residues 1–3,1 (SEQ ID NO: 2);

FIG. 3 shows the structure of [$Leu^{27}$]cyclo($Glu^{22}$-$Lys^{26}$)-hPTH-(1–28)-$NH_2$ (SEQ ID NO: 3);

FIG. 4 shows the structure of [$Leu^{27}$]cyclo($Glu^{22}$-$Lys^{26}$)-hPTH-(1–29)-$NH_2$ (SEQ ID NO: 4);

FIG. 5 shows the structure of [$Glu^{17}$, $Leu^{27}$]cyclo($Lys^{13}$-$Glu^{17}$, $Glu^{22}$-$Lys^{26}$)-hPTH-(1–31)-$NH_2$ (SEQ ID NO: 5);

FIG. 6 shows the structure of [$Glu^{17}$, $Leu^{27}$]cyclo($Lys^{13}$-$Glu^{17}$, $Glu^{22}$-$Lys^{26}$)-hPTH-(1–28)-NH2 (SEQ ID NO:6);

PREPARATION OF HORMONE ANALOGUES

Figure 7:
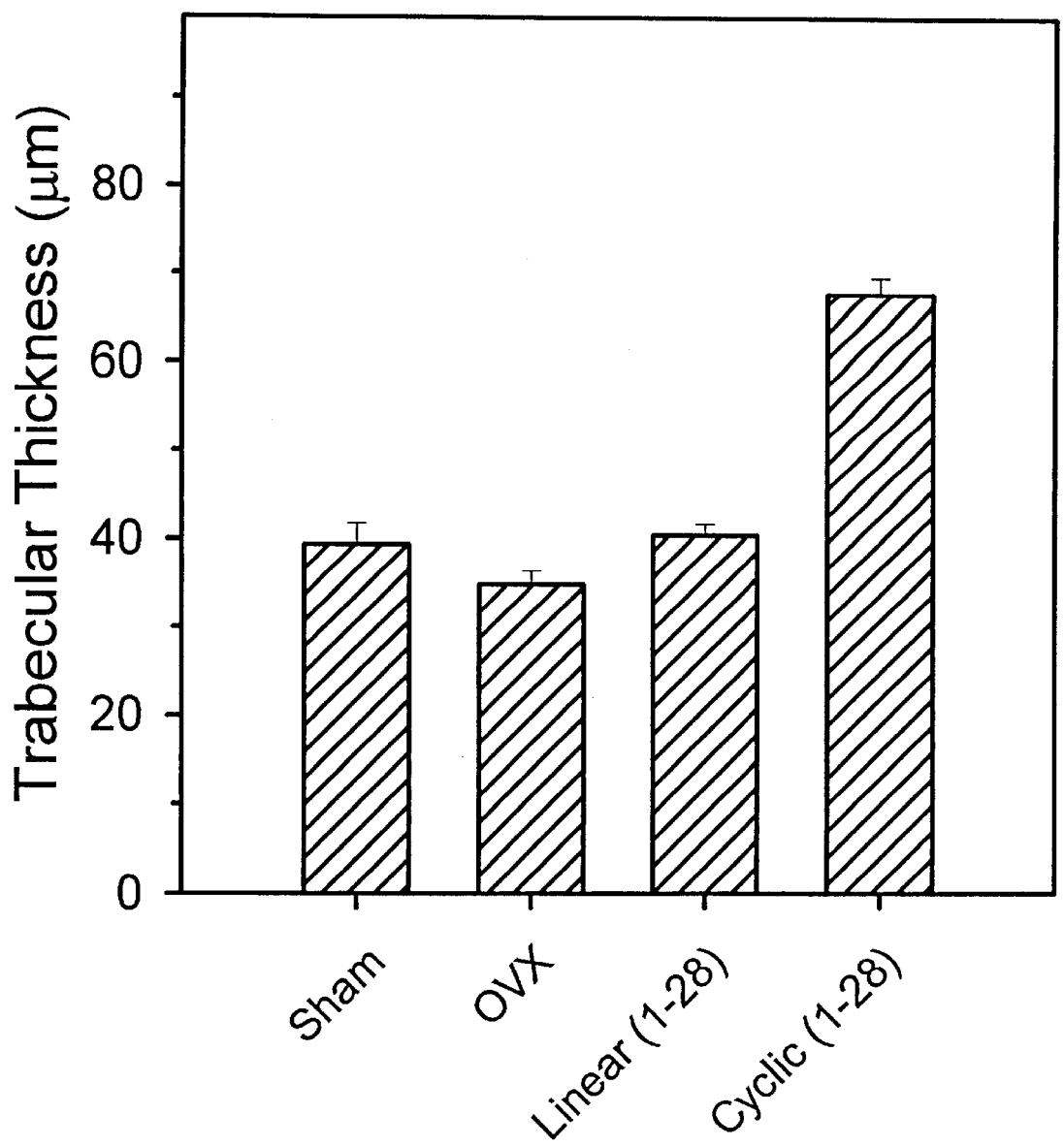
FIG. 7 shows the anabolic activity of the (1–28) cyclic analogues according to the invention, expressed in terms of trabecular bone thickness.

The technique of solid phase peptide synthesis developed by R. B. Merrifield ("Solid-Phase Peptide Synthesis", Advances in Enzymology 32, 221–296, 1969), incorporated herein by reference, is widely and successfully used for the synthesis of polypeptides such as parathyroid hormone. The strategy is based on having the carboxyl-terminus amino acid of the peptide attached to a solid support. Successive amino acids are then added in high yield. The N-terminal α-amino group is protected in such a way that this protecting group can be removed without removal of the peptide from the solic support. The chemistry used here involves a modification of the original Merrifield method, referred to as the Fmoc approach. The Fmoc (fluorenylmethoxycarbonyl) group can be removed by mild alkaline conditions, which leaves the alkali stable side-chain protecting groups and the link to the support untouched. This technique is described by E. Atherton and R. C. Sheppard, "Solid Phase Peptide Synthesis: a Practical Approach", IRL Press, New York, N.Y., incorporated herein by reference.

The analogues of the present invention may be administered to a warm-blooded mammal, in need thereof, particularly a human, by parenteral, topical, or rectal administration, or by inhalation or by oral delivery. The analogues may be conventionally formulated in a parenteral dosage form compounding about 1 to about 300 mg per unit of dosage with a conventional vehicle, excipient, binder, preservative, stabilizer, color, agent or the like as called for by accepted pharmaceutical practice.

For parenteral administration, a 1 to 2 ml painless subcutaneous injection through an ultra-fine 30-guage syringe needle would need to be given no more than once daily, for one to 2 years, depending on the severity of the disease. The injected material would contain one of the present invention in an aqueous, isotonic, sterile solution or suspension (optionally with a preservative such as phenol or a solubilizing agent such as ethylenediamine tetraacetic acid (EDTA)). Among the acceptable vehicles and solvents that may be employed are water, mildly acidified water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as a fixed oil in the preparation of injectables.

For rectal administration, the analogues of the present invention can be prepared in the form of suppositories by mixing with a suitable non-irritating excipient such as cocoa butter or polyethylene glycols.

For topical use, the analogues of the present invention can be prepared in the form of ointments, jellies, solutions, suspensions or dermal adhesive patches.

For inhalation, this can be achieved, for example, by means described in PCT published application no. W094/07514, the disclosure of which is incorporated herein by reference.

The daily dose should not have to exceed 0.05 mg/kg of body weight, or about 3.5 mg/ 70 kg human, depending on the activity of the specific compound, the age, weight, sex, and conditions of the subject being treated.

As would be well known, the amount of active ingredient that may be combined with the carded materials to produce a single dosage will vary depending upon the host treated and the particular mode of administration.

EXAMPLES

Example 1

Synthesis of [Leu$^{27}$]c(Glu$^{22}$-Lys$^{26}$)hPTH(1–28)NH$_2$ and [Leu$^{27}$]c(Glu$^{22}$-Lys$^{26}$)hPTH(1–29)NH$_2$:

This peptide was synthesized as described in Barbier, J. R., Neugebauer, W., Morley, P., Ross, V., Soska, M., Whitfield, J. F., and Willick, G. (1997) Bioactivities and secondary structures of constrained analogues of human parathyroid hormone: cyclic lactams of the receptor binding region. *J. Med. Chem.* 40, 1373–1380). Glu-22 and Lys-26, the residues to be cyclized, were protected orthogonally as the allyl ester and alloc derivative, respectively. Cyclisation was performed after addition of residue-17. The product was purified to greater than 97% by chromatography on a C$_{18}$ silica column (Vydac), eluted with a 1%/min. gradient of acetonitrile in 0.1% trifluoroacetic acid in water. The observed molecular weights are shown in Table 1 below.

Example 2

Synthesis of [Glu$^{17}$,Leu$^{27}$]c(Lys$^{13}$-Glu$^{17}$,Glu$^{22}$-Lys$^{26}$)hPTH(1–31)NH$_2$;

This synthesis was performed in a similar manner to the analogs of Example 1. Lys-13 was protected with an alloc group, and Glu-17 as an allyl ester. The first cyclisation was completed after addition of residue-17, and the cyclisation between residues 13 and 17 was carried out after completion of the entire synthesis, but before cleavage from the supporting resin and deprotection of side groups other than Lys-13 and Glu-17. The observed molecular weights are shown in Table 1 below.

TABLE 1

Masses of Synthetic Analogues of hPTH

| Analogue | M + 1 (expected) | M + 1 (observed) |
|---|---|---|
| [Leu$^{27}$]c(Glu$^{22}$-Lys$^{26}$)hPTH(1–29)NH$_2$ | 3471.2 | 3470.6 (±0.8) |
| [Leu$^{27}$]c(Glu$^{22}$-Lys$^{25}$)hPTH(1–28)NH$_2$ | 3343.1 | 3342.6 (±0.5) |
| [Glu$^{17}$,Leu$^{27}$]c(Lys$^{13}$-Glu$^{17}$,Glu$^{22}$-Lys$^{26}$)hPTH(1–31)NH$_2$ | 3709.5 | 3709.3 (±0.6) |

Example 3

Adenylyl cyclase activating activities

Adenylyl cyclase activities of 4- to 5-day cultures of ROS 17/2 cells in 24-well plates were estimated from the rate of formation of [$^3$H]-cAMF from the cellular ATP pool, which had been labelled with [$^3$H]-adenine before exposure to hPTH or its analogues in accordance with Jouishomme, H. Whitfield, J. F.; Gagnon, L.; Maclean, S.; Isaacs, R.; Chakravarthy, B.; Durkin, J.; Neugebauer, W.; Willick, G.; Rixon, R. H. Further Definition of the Protein Kinase C Activation Domain of the Parathyroid Hormone. *J. Bone Miner. Res.* 1994, 9, 943–949. The adenylyl cyclase activities, as concentrations of an analog required to obtain half-maximal activity (ED$_{50}$%), are shown in Table 2 below.

TABLE 2

AC-Stimulating Activities of Synthetic Analogues of hPTH

| Analogue | AC-Stimulation (ED$_{50\%}$, nM) |
|---|---|
| hPTH(1–29)NH$_2$ | 24 |
| hPTH(1–28)NH$_2$ | 24 |
| [Leu$^{27}$]c(Glu$^{22}$-Lys$^{26}$)hPTH(1–29)NH$_2$ | 8.4 |
| [Leu$^{27}$]c(Glu$^{22}$-Lys$^{26}$)hPTH(1–28)NH$_2$ | 9.6 |
| [Glu$^{17}$,Leu$^{27}$]c(Lys$^{13}$-Glu$^{17}$,Glu$^{22}$-Lys$^{26}$)hPTH(1–31)NH$_2$ | 13.2 |

Example 4

Anabolic activity of [Leu$^{27}$]c(Gul$^{22}$-Lys$^{26}$)hPTH (1–28)NH$_2$ in ovairiectomized rat model for osteoporosis Normal, sham-OVXed and OVXed Sprague-Dawley rats (3-months, sexually mature) were bought from Charles River Breeding Laboratories (St.Constant, QC, Canada). They were randomly separated into groups of 7–8 animals each (vehicle-injected sham-operated, vehicle-injected OVXed, OVXed injected with 5 nmoles of hPTH-(1–28)NH$_2$/100 g of body weight, OVXed injected with 25 nmoles of hPTH-(1–28)NH$_2$/100 g of body weight, and OVXed injected with 5 nmoles of [Leu$^{27}$]cyclo(Glu$^{22}$-Lys$^{26}$)hPTH-(1–28)NH$_2$/100 g of body weight). The animals were fed Purina rat chow (1.0% calcium, 0.6% phosphorus) and had free access to water.

This experiment used a preventative protocol in which the subcutaneous injections of peptide dissolved in an acidic saline vehicle (0.15M NaCl in water containing 0.001 HCl) were started at the end of the $2^{nd}$ week after OVX before a significant trabecular loss would have started and then given once each day, 6 days per week for the next 6 weeks (i.e., until the end of the $8^{th}$ week after OVX).

At the end of the experiment the femurs and L5 vertebrae were removed from the euthanized animals and cleaned. The vertebrae and the cistal halves of the femurs minus their epiphyses were fixed in acetate-buffer 10% formalin for 1 week and then demineralized by stirring in 5% trichloroacetic acid for 9–12 days, dehydrated, cleared, and embedded in paraffin wax. Serial 8-μm-thick transverse sections of the dehydrated, cleared, paraffin-embedded L5 vertebral bodies and 10-μm-thick longitudinal sections of the paraffin-embedded distal femur halves were cut with a Leica RM-2035 microtome and stained for 2 min at 55° C. with Sanderson's rapid bone stain (Surgipath Medical Industries Inc., Winnipeg, MB, Canada).

The abilities of the hPTH fragments to stimulate trabecular growth in the vertebrae and distal femurs were assessed by measuring the mean trabecular thicknesses (area $\mu m^2$]/perimeter [$\mu m$] of about 80 measurements per bone). The trabecular areas and perimeters were measured with a M4 imaging system from Imaging research Inc (St.Catherine's, ON, Canada). The software used for these analyses was Imaging Research's morphometry version 3.01.7. All of the histomorphometric measurements were made by the same 'blinded' observer for either the distal femurs or the L5 vertebrae.

Bone data were expressed as means ± SEMs. Statistical comparisons were made by one-way analysis of variance (ANOVA). Scheffe's test was used for multiple comparisons and p<0.05 was considered to be significant.

FIG. 7 shows the trabecular thicknesses of the sham, OVXed, and OVXed treated with 5 nmol/100 g body weight of linear hPTH(1–28)NH$_2$ (linear (1–28)) or [Leu$^{27}$]c(Glu$^{22}$-Lys$^{26}$)hPTH(1–28)NH$_2$ (cyclic(1–28)). Bone restoration with the linear molecule required a much larger dose, 25 nmol/100 g body weight (data not shown) than with the cyclized analog.

Example 5

The ability of [Glu$^{17}$,Leu$^{27}$]cyclo(Lys$^{13}$-Glu$^{17}$,Glu$^{22}$-Lys$^{26}$)hPTH(1–31)NH$_2$ to stimulate the growth of trabeculae in the distal femurs of ovariectomized (OVX) rats.

Figure 8:
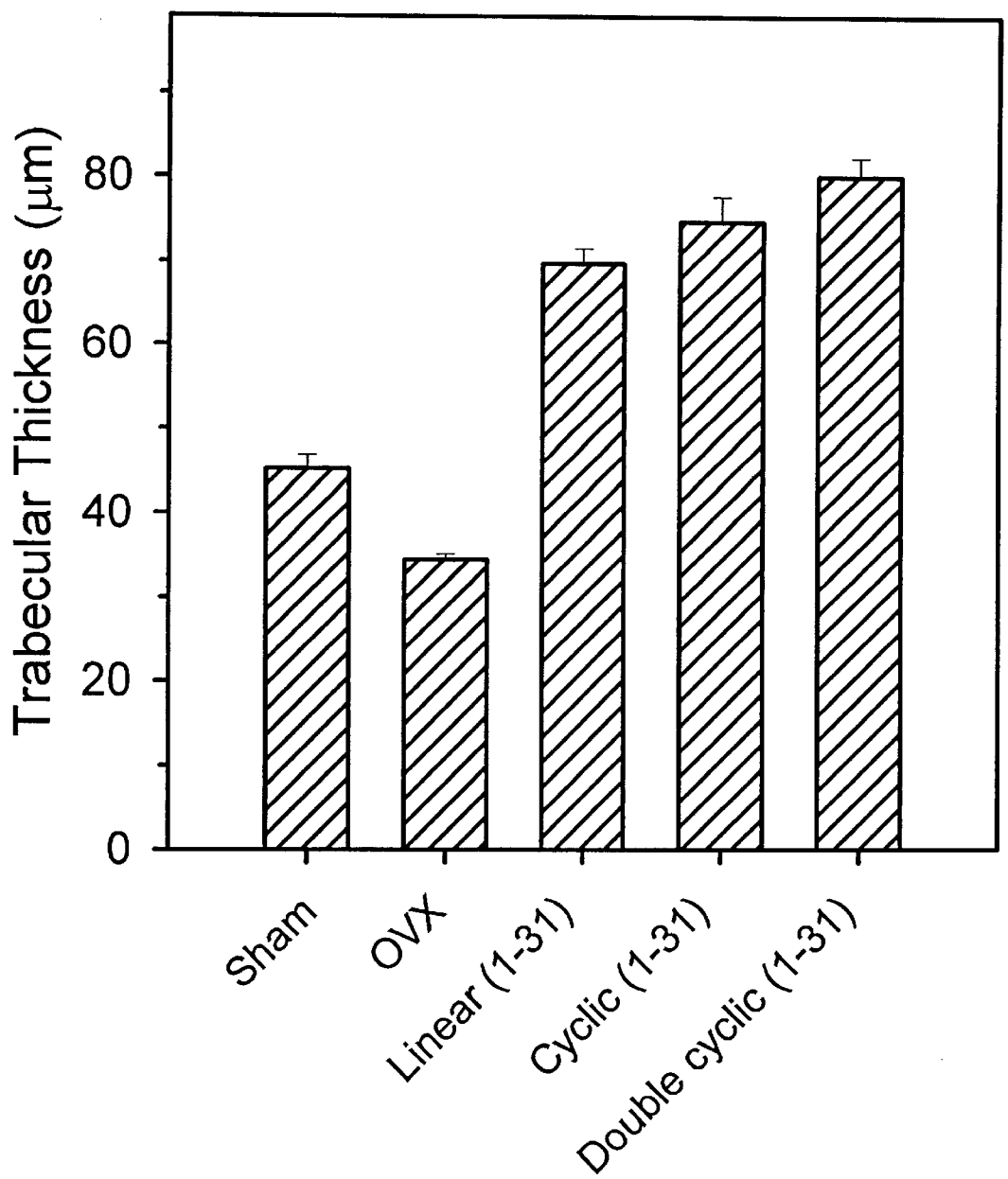
FIG. 8 shows the anabolic activity of the double cyclic analogues according to the invention, expressed in terms of trabecular bone thickness.

Rats were OVXed (OVX) or sham-OVXed (sham) and given daily subcutaneous injections of vehicle between the end of the $9^{th}$ week and the end of the $15^{th}$ week after OVX. Injection quantities were 5 nmoles/100 g of body weight. OVXed rats received daily subcutaneous injections of: vehicle (OVX), hPTH(1–31)NH$_2$, 5 nmol (linear), [Leu$^{27}$] cyclo(Glu$^{22}$-Lys$^{26}$)hPTH(1–28)NH$_2$, 5 nmol (cyclic), or [Glu$^{17}$,Leu$^{27}$]cyclo(Lys$^{13}$-Glu$^{17}$,Glu$^{22}$Lys$^{26}$)hPTH(1–31) NH$_2$, 5nmol(double cyclic). The femurs were demineralized and stained with Sanderson's rapid bone stain. As seen in FIG. 8, the double cyclic analog, [Glu$^{17}$,Leu$^{27}$]cyclo(Lys$^{13}$-Glu$^{17}$,Glu$^{22}$-Lys$^{26}$)hPTH(1–31)NH$_2$ was better than its monocyclic counterpart, [Leu$^{27}$]cyclo(Glu$^{22}$-Lys$^{26}$)hPTH (1–31)NH$_2$, and both were significantly better than the linear molecule, hPTH(1–31)NH$_2$, in increasing the thickness of the remaining trabeculae. This improvement is not correlated with their relative AC-stimulating activities, but likely results from greater stability to proteolytic attack and greater ability to be transported from the site of injection.

The double cyclic analogs of hPTH(1–28)NH$_2$, hPTH (1–29)NH$_2$, and hPTH(1–30)NH$_2$ are also expected to have improved bioactivities compared to linear and monocyclic forms.

REFERENCES

The disclosures of the following references are incorporate herein by reference.

(1) Caulfield, M. P.; McKee, R. L.; Goldman, M. E.; Duong, L. T.; Fisher, J. E.; Gay, C. T.; DeHaven, P. A,; Levy, J. J.; Roubini, E.; Nutt, R. F.; Chorev, M.; Rosenblatt, M. The Bovine Renal Parathyroid Hormone(PTH) Receptor Has Equal Affinity for 2 Different Amino Acid Sequences— The Receptor Binding Domains of PTH and PTH-Related Protein Are Located Within the 14–34 Region. *Endocrinology* 1990, 127, 83–87.

(2) Neugebauer, W.; Barbier, J.-R.; Sung, W. L.; Whitfield, J. F.; Willick, G. E. Solution Structure and Adenylyl Cyclase Stimulating Activities of C-Terminal Truncated Human Parathyroid Hormone Analogues *Biochemistry* 1995, 34, 8835–8842.

(3) Gardella, T. J.; Wilson, A. K.; Keutmann, H. T.; Oberstein, R.; Potts, J. T.; Kronenberg, H. M., and Nussbaum, S. R. Analysis of Parathyroid Hormone's Principal Receptor-Binding Region by Site-Directed Mutagenesis and Analog Design. *Endocrinology* 1993, 132, 2024–2030.

What is claimed is:

1. A human parathyroid hormone (hPTH) analogue or pharmaceutically acceptable salts thereof, having the amino acid sequence R-NH-R1-Val-Ser-Glu-Ile-Gln-Leu-R8-His-Asn-Leu-Gly-R13-R14-R15-R16-R17-R18-Glu-Arg-Val-R22-Trp-Leu-R25-R26-R27-Leu-Y (SEQ ID NO: 7) wherein, R=hydrogen or any linear or branched chain alkyl, acyl or aryl group,
R1=Ser, Ala or Aib,
R8=Met, Nle or a naturally occurring hydrophobic amino acid,
R13=Lys, Orn, Glu, Asp, Cys or Hcys,
R14=His or a water soluble amino acid,
R15=Leu or a water soluble amino acid,
R16=Asn or a water soluble amino acid,
R17=Ser, Glu, Asp, Lys, Orn, Cys, Hcys or a water soluble amino acid,
R18=Met, Nle or a naturally occuring hydrophobic amino acid,
R22=Glu, Lys, Orn, Cys, Asp or Hcys(homocysteine),
R25=Arg or His,
R26=Lys, Orn, Glu, Cys, Asp or Hcys,
R27=Lys, Leu or a naturally occurring hydrophobic or polar amino acid,
Y=X, Gln-X, Gln-Asp-X, or Gln-Asp-Val-X,
X=OR or NHR,
provided that when Y=X or Y=Gln-X, cyclized between one or two amino acid pairs R13 and R17 and R22 and R26, and when Y=Gln-Asp-X or Y=Gln-Asp-Val-X, cyclized between two amino acid pairs R13 and R17 and R22 and R26, each amino acid in said amino acid pairs having a side chain enabling the formation of either a lactam or a disulfide bridge between the side chains thereof.

2. An analogue according to claim 1, wherein the cyclisation is in the form of a lactam.

3. An analogue according to claim 2, including a R22-R26 lactam.

4. An analogue according to claim 3, including a Glu22-Lys26 lactam.

5. An analogue according to claim 1, wherein R is H and X is $NH_2$.

6. An analogue according to claim 5, wherein R27 is Lys or Leu.

7. A human parathyroid hPTH analogue or pharmaceutically acceptable salts thereof, having the amino acid sequence R-NH-Ser-Val-Ser-Glu-Ile-Gln-Leu-R8-His-Asn-Leu-Gly-Lys-His-Leu-Asn-Ser-R18-Glu-Arg-Val-R22-Trp-Leu-R25-R26-R27-Leu-Y (SEQ ID NO: 8) wherein, R=hydrogen or any linear or branched chain alkyl, acyl, or aryl group,
R8=Met or Nle,
R18=Met or Nle,
R22=Glu, Asp, Lys, Orn, Cys or Hcys,
R25=Arg or His,
R26=Glu, Asp, Lys, Orn, Cys or Hcys,
R27=Lys, Leu, Ala or Nle,
Y=X or Gln-X, and
X=OR or NHR,
cyclized between amino acid pairs R22 and R26, each amino acid in said amino acids pairs having a side chain enabling the formation of either a lactam or a disulfide bridge between the side chains thereof.

8. An analogue according to claim 7, wherein R27 is Lys or Leu.

9. An analogue according to claim 8, including a Glu22-Lys26 lactam.

10. An analogue according to claim 7, having the SEQ ID NO: 3.

11. An analogue according to claim 7, having the SEQ ID NO: 4.

12. A human parathyroid hormone(hPTH) analogue or pharmaceutically acceptable salts thereof are provided, having the amino acid sequence RNH-Ser-Val-Ser-Glu-Ile-Gln-Leu-R8-His-Asn-Leu-Gly-R13-His-Leu-Asn-R17-R18-Glu-Arg-Val-R22-Trp-Leu-R25-R26-R27-Leu-Y (SEQ ID NO: 9) wherein, R=hydrogen or any linear or branched chain alkyl, acyl or aryl group,
R8=Met or Nle,
R13=Lys, Orn, Glu, Asp, Cys or Hcys,
R17=Lys, Orn, Glu, Asp, Cys or Hcys,
R18=Met or Nle,
R22=Glu, Asp, Lys, Orn, Cys or Hcys,
R25=Arg or His,
R26=Lys, Orn, Glu, Asp, Cys or Hcys,
R27=Lys, Leu, Nle or a naturally occurring hydrophobic or polar amino acid,
Y=X, Gln-X, Gln-Asp-X or Gln-Asp-Val-X,
X=OR or NHR,
cyclysed between two amino acid pairs R13 and R17 and R22 and R26, each amino acid residue R13 and R17 having a side chain which enables formation of either a lactam or a disulfide bridge between the side chains thereof, and each amino acid residue R22 and R26 having a side chain which enables formation of either a lactam or a disulfide bridge between the side chains thereof.

13. An analogue according to claim 12, wherein R27 is Lys or Leu.

14. An analogue according to claim 13, including a Glu22-Lys26 lactam.

15. An analogue according to claim 12, having the SEQ ID NO: 5.

16. An analogue according to claim 12, having the SEQ ID NO: 6.

17. A composition for administration to a warm-blooded animal in need thereof, comprising a human parathyroid hormone(hPTH) analogue according to claim 1, in association with a pharmaceutically acceptable carrier or excipient.

18. A method of treating a warm-blooded animal in need of such treatment, comprising administering to such warm-blooded animal, a therapeutically effective amount of a human parathyroid hormone(hPTH) analogue according to claim 1.

19. A method according to claim 18, wherein the analogue has the SEQ ID NO: 3.

20. A method according to claim 18, wherein the analogue has the SEQ ID NO: 4.

21. A method according to claim 18, wherein the analogue has the SEQ ID NO: 5.

22. A method according to claim 18, wherein the analogue has the SEQ ID NO: 6.

\* \* \* \* \*